United States Patent [19]

D'Silva

[11] Patent Number: 4,657,904

[45] Date of Patent: Apr. 14, 1987

[54] SULFUR-CONTAINING BIS-IMINO CARBAMATE COMPOUNDS, PESTICIDAL COMPOSITION AND USE

[75] Inventor: Themistocles D. J. D'Silva, South Charleston, W. Va.

[73] Assignee: Union Carbide Corporation, Danbury, Conn.

[21] Appl. No.: 864,274

[22] Filed: May 19, 1986

Related U.S. Application Data

[62] Division of Ser. No. 389,980, Jun. 18, 1982, Pat. No. 4,612,426, which is a division of Ser. No. 957,561, Nov. 3, 1978, Pat. No. 4,435,421.

[51] Int. Cl.⁴ .................. A01N 47/24; C07D 295/22

[52] U.S. Cl. .................... 514/229; 514/315; 514/424; 544/159; 546/247; 548/542

[58] Field of Search .............. 544/159; 546/247; 548/542; 514/229, 315, 424

[56] References Cited

U.S. PATENT DOCUMENTS 4,059,623  11/1977  Belling ........................ 544/164
4,108,991  8/1978   Fukuto et al. ................ 546/247
4,153,611  5/1979   Asato .......................... 549/57

*Primary Examiner*—Robert W. Ramsuer
*Attorney, Agent, or Firm*—Gerald L. Coon

[57] ABSTRACT

Sulfur-containing bis-amino carbamate compounds exhibit outstanding acaricidal, nematocidal and insecticidal activity.

3 Claims, No Drawings

SULFUR-CONTAINING BIS-IMINO CARBAMATE COMPOUNDS, PESTICIDAL COMPOSITION AND USE

This application is a division of prior U.S. application Ser. No. 389,980, filing date June 18, 1982, now U.S. Pat. No. 4,612,426, which is a division of application Ser. No. 957,561, filing date Nov. 3, 1978, now U.S. Pat. No. 4,435,421.

This invention relates to methods and compositions for controlling insect, acarid and nematode pests. In another aspect, this invention relates to novel carbamate compounds and to their methods of preparation.

The compounds which are employed as the active ingredients in the pesticidal compositions of this invention are compounds of the following general formula:

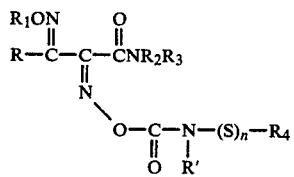

wherein:
n=1 or 2;
R, R', $R_1$, $R_2$, and $R_3$ are individually alkyl groups of one to four carbon atoms;
$R_4$ is:
- (a) $C_1$-$C_{18}$ alkyl, $C_3$-$C_8$ cycloalkyl, or dialkylamino group; or
- (b) piperidino, pyrrolidino or morpholino group each of which may be unsubstituted or substituted with one or two alkyl groups; or
- (c) a phenyl group which may be unsubstituted or substituted with one or more alkyl, chloro, fluoro, cyano, nitro, alkoxy, trifluoromethyl, alkylthio, alkylsulfinyl, alkylsulfonyl, alkoxyalkyl, alkylthioalkyl, alkylsulfinylalkyl, alkylsulfonylalkyl or dialkylamino groups; or
- (d) a group of the formula:

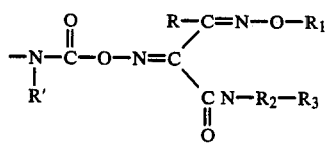

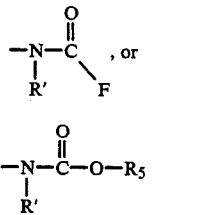

wherein: $R_5$ is:
(1) an alkyl, alkoxyalkyl, or phenylalkyl group; or
(2) a phenyl group which may be unsubstituted or substituted with one or more $C_1$-$C_{12}$ alkyl, chloro, fluoro, alkoxy, alkylthio, alkylthioalkyl, alkylsulfinyl, alkylsulfinylalkyl, alkylsulfonyl, alkylsulfonylalkyl, alkynyloxy, dialkylamino, alkoxyamino, formamidino, cyano, dioxolanyl or dithiolanyl groups in any combination; or
(3) a naphthyl, tetrahydronaphthyl, dihydrobenzofuranyl, benzodioxolanyl, or benzothienyl group all of which may be unsubstituted or substituted with one or more alkyl groups; or
(4) a group of the formula:

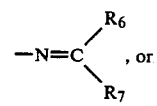

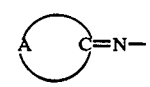

wherein:
$R_6$ is a chloro, alkyl, alkylthio, cyanoalkylthio, amidoalkylthio or cyano group; or $R_6$ is hydrogen provided $R_7$ is not hydrogen;
$R_7$ is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, or phenyl group, said phenyl group may be unsubstituted or substituted with one or more alkyl, chloro, or fluoro groups in any combination; or $R_7$ is hydrogen, provided $R_6$ is not hydrogen;
A is a divalent aliphatic chain completing a five or six membered heterocyclic ring structure, said aliphatic chain having from 2 to 24 aliphatic carbon atoms, said ring structure may include in any combination one, two or three divalent oxygen, sulfur, sulfinyl, or sulfonyl groups and may further include one group selected from a divalent amino group, a $C_1$-$C_8$ divalent alkylamino group, or a divalent carbonyl group;
provided that except when $R_4$ is an alkyl group or when $R_5$ is a phenyl group substituted with an alkyl group, no single alkyl or alkylene moiety in any $R_4$, $R_5$, $R_6$, or $R_7$ group may include more than eight carbon atoms.

DESCRIPTION OF THE PREFERRED EMBODIMENT

All compounds within the purview of the above generic formula exhibit pesticidal activity to a lesser or greater extent. Some of these compounds exhibit very powerful pesticidal activity in extremely small dosages while others require larger dosages to be pesticidally effective.

In addition, these compounds are relatively non-phytotoxic and relatively non-toxic to mammals when used in amounts sufficient to kill plant pests.

Preferred because of their higher level of pesticidal activity are the compounds of this invention wherein the substituents are defined as follows:

R, R', $R_1$, $R_2$, and $R_3$ are individually methyl groups;
$R_4$ is:
1. $C_1$-$C_{18}$ alkyl, alkyl substituted phenyl, or morpholino group; or
2. a group of the formula:

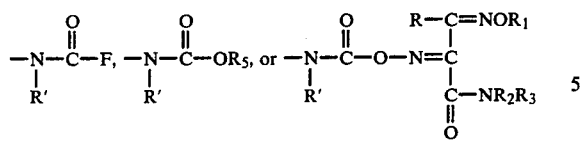

$R_5$ is:
(1) a phenyl group which may be unsubstituted or substituted with one of the following groups: $C_1-C_{12}$ alkyl, dialkylamino, alkoxy, alkylthio, alkylthioalkyl, dioxolanyl or dithiolanyl group; or
(2) naphthyl, tetrahydronaphthyl, dihydrobenzofuranyl, all of which may be unsubstituted or substituted by up to two alkyl groups; or
(3) a group of the formula:

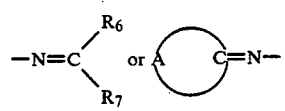

$R_6$ is hydrogen, alkylthio, alkyl or cyanoalkylthio.
$R_7$ is alkyl, alkylthio, alkoxycarbonyl, dialkylaminocarbonyl, alkylthioalkyl, cyanoalkyl or alkylsulfonylalkyl.

A is a divalent aliphatic chain completing a five or six membered heterocyclic ring structure, said aliphatic chain having from 2 to 24 aliphatic carbon atoms, said ring structure may include in any combination one or two divalent oxygen, sulfur, sulfinyl, or sulfonyl groups and may also include one group selected from a divalent amino group, a $C_1-C_8$ divalent alkylamino group, a $C_1-C_8$ divalent alkylimino group, or a carbonyl group.

Examples of preferred ring structures when $R_5$ is

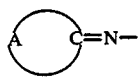

are: 2-oximino-1,4-dithianes, 2-oximino-1,3-dithianes, 4-oximino-1,3-dithiolanes, 2-oximino-1,4-dioxanes, 2-oximino-tetrahydro-1,4-thiazine-3-ones, 2-oximino-1,3-dithiolanes, 2-imino-4-oximino-1,3-dithiolanes, 3-oximinothiophanes, 2-oximinothiophanes, 2-oximino-tetrahydro-1,4-oxazine-3-ones, 2-oximino-1,4-oxathianes, 4-oximino-1,3 oxathiolanes, 2-oximino-thiazolidin-3-ones, 2-oximino-1,3-thiazolidin-4-ones or 2-oximino-tetrahydro-1,4-thiazin-5-ones, all of which may be optionally substituted by one to four alkyl groups and in said preferred ring structures sulfur may be in any of its oxidation states.

Most preferred are the compounds wherein:
R,R', $R_1,R_2$ and $R_3$ are individually methyl groups;
$R_4$ is $C_1-C_8$ alkyl, a tert-butyl substituted phenyl group, a morpholino group or the group of the formula:

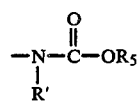

wherein:
$R_5$ is:

(a) a naphthyl group, a phenyl group substituted with one $C_1-C_9$ alkyl group, a dihydrobenzofuranyl group substituted with two methyl groups; or
(b) the group of the formula:

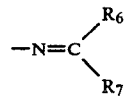

wherein: $R_6$ is $C_1-C_6$ alkylthio and $R_7$ is $C_1-C_6$ alkyl.

2-[[N'-methyl-N'-[N''-(1-naphthyloxycarbonyl)-N''-methylaminosulfenyl]-carbamoyloxy]]imino-3-methoxyimino-N,N-dimethylbutyramide and 2-[[N'-methyl-N'-[N''-(4-nonylphenyloxycarbonyl)-N''-methylaminosulfenyl]carbamoyloxy]]imino-3-methoxyimino-N,N-dimethylbutyramide are especially preferred compounds of the instant invention due to their combination of low mammalian toxicity, low phytotoxicity and pesticidal activity.

The compounds of this invention can be prepared in accordance with a variety of methods as illustrated by the following reaction schemes, wherein R, $R_1$, $R_2$, $R_3$, $R_4$, $R_5$, $R_6$, $R_7$, R' and n are as previously defined unless otherwise noted and X is fluorine or chlorine.

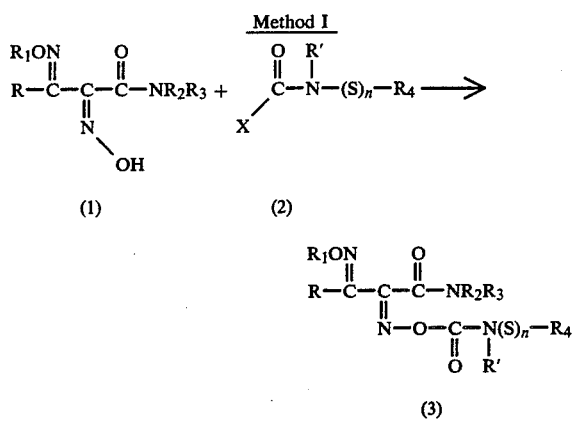

Method I is a reaction scheme that can be used to make any compound of the instant invention.

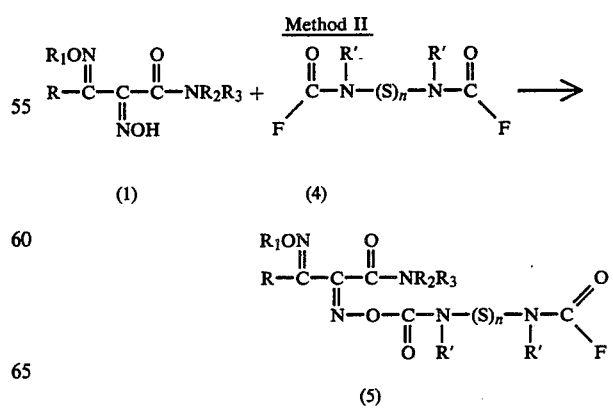

Method II is limited to compounds wherein $R_4$ is

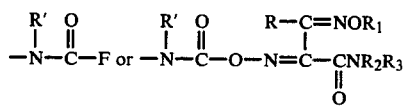

Method III

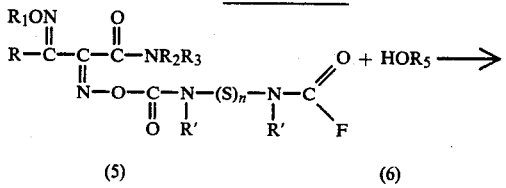

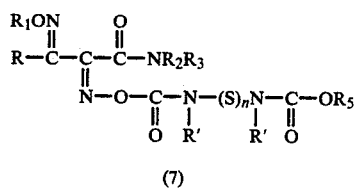

Method III is limited to compounds wherein R₄ is

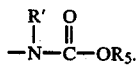

The reactions in Methods I, II and III are conducted in the presence of an acid acceptor, preferably in an inert solvent. Substantially equimolar amounts of an acid acceptor and the reactants are used although a slight excess of the acid acceptor may be used if desired. In Method II, if a symmetrical bis-carbamate sulfide or disulfide is desired the reaction may be carried out by using two equivalents of the oxime. compound (1), with one equivalent of the carbamoyl fluoride, compound (4), and two equivalents of the acid acceptor. The synthesis of these symmetrical compounds also may be accomplished in two steps. The first step consists of the reaction depicted in the reaction scheme of Method II, above. The second step consists of reacting the reaction product of Method II, compound (5), with the second equivalent of the oxime, compound (1) and the acid acceptor.

It should also be noted that although compound (5), above, the product of Method II, is itself a pesticidal compound of the instant invention, it is also capable of use as a reactant-intermediate in the synthesis of compounds according to Method III, above.

The acid acceptor utilized in the reactions of Methods I, II and III can be either an organic or an inorganic base. Illustrative of organic bases that are useful as acid acceptors in the conduct of these reactions are tertiary amines such as trimethylamine, triethylamine, pyridine or 1,4-diazabicyclo-[2.2.2]octane; or alkali methal alkoxides, as for example, sodium methoxide, sodium ethoxide, or the like. Bases such as sodium carbonate, sodium hydroxide or potassium hydroxide are illustrative of inorganic bases that are useful as acid acceptors. Preferred organic acid acceptors are tertiary amines such as triethylamine, pyridine or trimethylamine.

The reactions in Methods I to III can be conducted in organic solvents, in an aqueous solvent or in a two-phase mixture of organic and aqueous solvents. Illustrative of organic solvents which are generally suitable for use in the conduct of these reactions are saturated, unsaturated and aromatic hydrocarbons, e.g. hexane, cyclohexane, octane, dodecane, naptha, decalin, kerosene, cycloheptane, benzene, toluene, xylene, napthalene; ethers such as dioxane, tetrahydrofuran, diethyl ether, tetrahydropyran, 1,2-dimethoxybenzene, 1,2-diethylbenzene, the dialkyl ethers of ethylene glycol, of propylene glycol or chlorinated aliphatic hydrocarbons as, for example, chloroform, dichloromethane, 1,1-dichloroethane, carbon tetrachloride, or the like.

When an inorganic base is used in a heterogeneous phase-system or a homogeneous system, a phase transfer agent such as quaternary ammonium halides or crown ether compounds may be used to facilitate the transfer of the reactants across the phase interface or to improve the nucleophilicity of the oxime compound.

The reactions illustrated by the general schemes given above may also be conducted in a solvent which functions as an acid acceptor. Illustrative of such multifunctional solvents are N,N,-dimethylaniline, pyridine α-picoline, lutidine, collodine or like aromatic or heterocyclic tertiary amine compound.

The reactions illustrated by the general schemes given above are neither temperature nor pressure sensitive and can be conducted over a broad temperature and pressure range to yield the desired product. Generally these reactions are conducted at a temperature of from about −40° C. to about 120° C. preferably from about −10° C. to about 100° C. For convenience these reactions are conducted at atmospheric or autogeneous pressure.

The oxime compounds, reactant (1) above, utilized as reactants can be prepared according to the method described in German Pat. No. 2,428,070. The bis-carbamoyl fluorides can be prepared by reacting hydrogen fluoride with methyl isocyante to form N-methylcarbamoyl fluoride compound which is then reacted with sulfur dichloride or sulfur monochloride to form bis-(N-methyl-N-fluorocarbonylamino) sulfide or disulfide compounds. The preparation of these and other carbamoyl fluorides used in this invention is more fully described in U.S. Pat. Nos. 3,639,471; 3,998,963, Belgium Pat. Nos. 843,415; 848,914 and Netherland Pat. No. 7,508,068.

The following aracidical and herbicidal compounds are illustrative of the compounds of the instant invention:

(1) 2-[[N'-Methyl-N'-[N"'-(2-methyl-2-methylthio-propylideneiminooxycarbonyl)-N"-methylaminosulfenyl]carbamoyloxy]]-imino-3-methoxyimino-N,N-dimethylbutyramide (2) 2-[[N'-Methyl-N'-[N"'-(2-methyl-2-methylsulfonylpropylideneiminooxycarbonyl)-N"-methylaminosulfenyl]carbamoyloxy]]imino-3-methoxyimino-N,N-dimethylbutyramide (3) 2-[[N'-Methyl-N'-[N"'-(3,3-dimethyl-1-methylthio-2-butylideneiminooxycarbonyl)-N"-methylaminosulfenyl]carbamoyloxy]]imino-3-methoxyimino-N,N-dimethylbutyramide (4) 2-[[N'-Methyl-N'-[N"'-(1-(2-cyanoethylthio)e-thylideneimino-oxycarbonyl)-N"'-methylaminosulfenyl]carbamoyloxy]]imino-3-methoxyimino-N,N-dimethylbutyramide (5) 2-[[N'-Methyl-N'-[N"'-(1,3-dithiolane-2-ylideneiminooxycarbonyl)-N"'-methylaminosulfenyl]carbamoyloxy]]imino-3-methoxyimino-N,N-dimethylbutyramide (6) 2-[[N'-Methyl-N'-[N''-(1,4-dithiane-2-ylideneiminooxycarbonyl)-N''-methylaminosulfenyl]carbamoyloxyl]]imino-3-methoxyimino-N,N-dimethylbutyramide (7) 2-[[N'-Methyl-N'-[N''-(dimethylaminocarbonyl-methylthiomethylideneiminooxycarbonyl)-N''-Methylaminosulfenyl]carbamoyloxy]]imino-3-methoxyimino-N,N-dimethylbutyramide (8) 2-[[N'-Methyl-N'-[N''-(4-methyl-tetrahydro-1,4-thiazine-3-one-2-ylideneimino-oxycarbonyl)-N''-methylaminosulfenyl]carbamoyloxy]]imino-3-methoxyimino-N,N-dimethylbutyramide (9) 2-[[N'-Methyl-N'-[N''-(4,5,5-trimethyl-thiazolidin-3-one-2-ylideneiminooxycarbonyl)-N''-methylaminosulfenyl]carbamoyloxy]]imino-3-methoxyimino-N,N-dimethylbutyramide

(10) 2-[[N'-Methyl-N'-[N''-(3,5,5-trimethyl-thiazolidin-4-one-2-ylideneiminooxycarbonyl)-N''-methylaminosulfenyl]carbamoyloxy]]imino-3-methoxyimino-N,N-dimethylbutyramide

(11) 2-[[N'-Methyl-N'-[N''-(5-methyl-1,3-oxathiolane-2-ylideneiminooxycarbonyl)-N''-methylaminosulfenyl]carbamoyloxy]]imino-3-methoxyimino-N,N-dimethylbutyramide

(12) 2-[[N'-Methyl-N'-[N''-(3,3-dimethyl-1,4-dioxane-2-ylideneiminooxycarbonyl)-N''-methylaminosulfenyl]carbamoyloxy]]imino-3-methoxyimino-N,N-dimethylbutyramide

(13) 2-[[N'-Methyl-N'-[N''-(3-methyl-4-methylthiophenyloxycarbonyl)-N''-methylaminosulfenyl]carbamoyloxy]]imino-3-methoxyimino-N,N-dimethylbutyramide

(14) 2-[[N'-Methyl-N'-[N''-(3,5-dimethyl-4-dimethylaminophenyloxycarbonyl)-N''-methylaminosulfenyl]carbamoyloxy]]imino-3-methoxyimino-N,N-dimethylbutyramide

(15) 2-[[N'-Methyl-N'-[N''-(2,2-dimethylbenzodioxalanyl-4-oxycarbonyl)-N''-methylaminosulfenyl]carbamoyloxy]]imino-3-methoxyimino-N,N-dimethylbutyramide

(16) 2-[[N'-Methyl-N'-[N''-(2-ethylthiomethylphenyloxycarbonyl)-N''-methylaminosulfenyl]carbamoyloxy]]imino-3-methoxyimino-N,N-dimethylbutyramide

(17) 2-[[N'-Methyl-N'-[N''-(4-nitrophenyloxycarbonyl)-N''-methylaminosulfenyl]carbamoyloxy]]imino-3-methoxyimino-N,N-dimethylbutyramide

(18) 2-[[N'-Methyl-N'-[N''-(2-isopropoxyphenyloxycarbonyl)-N''-methylaminosulfenyl]carbamoyloxy]]imino-3-methoxyimino-N,N-dimethylbutyramide

(19) 2-[[N'-Methyl-N'-[N''(2-(1,3-dioxalanyl)-2-phenyloxycarbonyl)-N''-methylaminosulfenyl]carbamoyloxy]]imino-3-methoxyimino-N,N-dimethylbutyramide

(20) 2-[[N'-Methyl-N'-[N''-(2-(1,3-dithiolanyl)-2-phenoxycarbonyl)-N''-methylaminosulfenyl]carbamoyloxy]]imino-3-methoxyimino-N,N-dimethylbutyramide

(21) 2-[[N'-Methyl-N'-[N''-(2-cyano-2-methyl-propylideneiminooxycarbonyl)-N''-methylaminosulfenyl]carbamoyloxy]]imino-3-methoxyimino-N,N-dimethylbutyramide

(22) 2-[[N'-Methyl-N'-[N''-(2-nitro-2-methyl-propylideneiminooxycarbonyl)-N''-methylaminosulfenyl]carbamoyloxy]]imino-3-methoxyimino-N,N-dimethylbutyramide

(23) 2-[[N'-Methyl-N'-[N'-4-cyano-2,2-dimethyl-butylideneiminooxycarbonyl)-N''-methylaminosulfenyl]carbamoyloxy]]imino-3-methoxyimino-N,N-dimethylbutyramide

(24) 2-[[N'-Methyl-N'[N''-(2-hydroxymethyl-2-methylpropylideneiminooxycarbonyl)-N''-methylaminosulfenyl]carbamoyloxy]]imino-3-methoxyimino-N,N-dimethylbutyramide

(25) 2-[[N'-Methyl-N'-[N''-(α-cyanobenzylideneiominooxycarbonyl)-N''-methylaminosulfenyl]carbamoyloxy]]imino-3-methoxyimino-N,N-dimethylbutyramide

(26) 2-[[N'-Methyl-N'-(2-chlorophenyloxycarbonyl)-N''-methylaminosulfenyl]carbamoyloxy]]imino-3-methoxyimino-N,N-dimethylbutyramide

(27) 2-[[N'-Methyl-N'-[N''-(2-propynyloxyphenyloxycarbonyl)-N''-methylaminosulfenyl]carbamoyloxy]]imino-3-methoxyimino-N,N-dimethylbutyramide

(28) 2-[[N'-Methyl-N'-[N''-(4-benzothienyloxycarbonyl)-N'-methylaminosulfenyl]carbamoyloxy]-]imino-3-methoxyimino-N,N-dimethylbutyramide

(29) 2-[[N'Methyl-N'-[N''-(3-isopropylphenyloxycarbonyl)-N''-methylaminosulfenyl]carbamoyloxy]-]imino-3-methoxyimino-N,N-dimethylbutyramide

(30) 2-[[N'-Methyl-N'-[N''-(3,4,5-trimethylphenyloxycarbonyl)-N''-methylaminosulfenyl]carbamoyloxy]]imino-3-methoxyimino-N,N-dimethylbutyramide

(31) 2-[[N'-Methyl-N'-[N''-(1,3,5-trithiane-2-ylideneiminooxycarbonyl)-N''-methylaminosulfenyl]carbamoyloxy]]imino-3-methoxyimino-N,N-dimethylbutyramide

(32) 2-[[N'-Methyl-N'-[N''-(1,3,5-oxadithiane-4-ylideneiminooxycarbonyl)-N''-methylaminosulfenyl]carbamoyloxyl]]imino-3-methoxyimino-N,N-dimethylbutyramide

(33) 2-[[N'-Methyl-N'-[N''-(4-methyl-tetrahydro-1,4-oxazine-3-one-2-ylideneimino-oxycarbonyl)-N''-methlaminosulfenyl]carbamoyloxy]]imino-3-methoxyimino-N,N-dimethylbutyramide

(34) 2-[[N'-Methyl-N'-[N''-(3-methylsulfonyl-2-butylideneiminooxycarbonyl)-N''-methylaminosulfenyl]carbamoyloxyl]]imino-3-methoxyimino-N,N-dimethylbutyramide

(35) 2-[[N'-Butyl-N'-[N''-(1-methylthioethylideneiminooxycarbonyl)-N''-butylaminosulfenyl]carbamoyloxy]]imino-3-butoxyimino-N,N-dibutylbutyramide

(36) 2-[[N'-Methyl-N'-[N''-(4-dodecyl phenyl oxycarbonyl)-N'-methylaminosulfenyl]carbamoyloxy]-]imino-3-methoxyimino-N,N-dimethylbutyramide

(37) 2-[[N'-Methyl-N'-[N''-4-nonylphenyloxycarbonyl)-N'-methylaminosulfenyl]carbamoyloxy]-]imino-3-methoxyimino-N,N-diethyl butyramide

(38) 2-[[N'-Methyl-N'-[N''-cyclohexylthiosulfenyl]-carbamoyloxy]]imino-3-methoxyimino-N,N-dimethylbutyramide The following examples are presented to more particularly illustrate this invention:

EXAMPLE I

Preparation of
2-[[N'-Methyl-N'-[4-tert-butylphenylsulfenyl]carbamoyloxy]]imino-3-methoxyimino-N,N-dimethylbutyramide To a solution of 5.6 g (0.03 m) of N,N-dimethyl-2-hydroxyimino-3-methoxyiminobutyramide and 7.23 g (0.03 m) of N-methyl-N-(4-tert-butylphenylsulfenylcarbamoyl fluoride in 200 ml of toluene was added with stirring 3.1 g (0.03 m) of triethylamine. After heating at 40° C. for 24 hrs, the reaction mixture was cooled, washed with water, dried over magnesium sulfate and concentrated under reduced pressure to afford 10 g of a viscous residual oil.

Calcd. for $C_{19}H_{28}N_4O_4S$: C, 55.9; H, 6.9; N, 13.7. Found: C, 56.5; H, 6.8; N, 13.1.

EXAMPLE II

Preparation of
2-[[N-Methyl-N'-[4-tetrahydro-1,4-oxazine)sulfenylcarbamoyloxy]]imino-3-methoxyimino-N,N-dimethyl butyramide To a solution of 5.6 g (0.03 m) of N,N-dimethyl-2-hydroxyimino-3-methoxyiminobutyramide and 5.8 g (0.03 m) of N-methyl-N-(4-morpholinosulfenyl)-carbamoyl fluoride in 200 ml of toluene was added 3.1 g of triethylamine. The reaction mixture was heated at 50° C. for six hours and then continued stirring at room temperature overnight. The mixture was washed with water and the toluene layer was dried over magnesium sulfate. Concentration under reduced pressure gave a residual solid. Recrystallization from isopropyl ether afforded 7.0 g of a white solid, m.p. 90°–91° C.

EXAMPLE III

Preparation of
2-[[N'-Methyl-N-[2-methyl-2-propanethiosulfenyl]carbamoyloxy]]imino-N,N-dimethyl-3-methoxyiminobutyramide To a solution of 6.0 g (0.321 m) of N,N-dimethyl-3-methoxyimino-2-oximinobutyramide and 6.33 g (0.321 m) of N-(2-methyl-2-propanethiosulfenyl)-N-methylcarbamoyl fluoride in 75 ml of dioxane was added with stirring 3.25 g (0.0321 m) of triethylamine. After stirring for 8 hrs. at ambient temperatures, the solution was concentrated under reduced pressure and diluted with ethyl acetate. The ethyl acetate solution was washed 4×75 ml water and dried over magnesium sulfate. On concentration it afforded 8.97 g of a crude viscous oil. Purification by dry column chromatography afforded a solid as a mixture of isomers. m.p. 100°–105° C.

EXAMPLE IV

Preparation of
2-[[N'-Methyl-N'-[N"-fluorocarbonyl-N"-methylaminosulfenyl]carbamoyloxy]]imino-3-methoxyimino-N,N-dimethylbutyramide To a solution of 22.0 g (0.12 m) of N,N'-bis-(N-methyl-N-fluorocarbonylamino) sulfide in 200 ml of toluene was added 12.0 g (0.12 m) of triethylamine followed by a slow addition of 22.4 g (0.12 m) of N,N-dimethyl-2-hydroxyimino-3-methoxyiminobutyramide dissolved in 100 ml of toluene. After stirring at room temperature for 20 hrs. the reaction mixture was washed with water and dried over anhydrous magnesium sulfate. Concentration under reduced pressure afforded an oil residue which solidified on standing. Crystallization from xylene afforded 12.0 g of white solid. m.p. 113°–116° C.

EXAMPLE V

Preparation of
2-[[N'-Methyl-N'-[N"-(1-methylthioethylideneiminooxycarbonyl)-N"-methylaminosulfenyl]carbamoyloxy]]imino-3-methoxyimino-N,N-dimethylbutyramide To a solution of 5.6 g (0.03 m) of N,N-dimethyl-2-hydroxyimino-3-methoxyiminobutyramide and 7.1 g (0.03 m) of S-methyl-N-[[N'-methyl-N'-[N"-fluoroformyl-N"-methylaminosulfenyl]carbamoyloxy]]thioacetimidate in 200 ml of toluene was added 4.0 g of triethylamine. The reaction mixture was stirred for 20 hrs at ambient temperatures and washed with water. The toluene layer was dried over anhydrous magnesium sulfate and concentrated under reduced pressure to afford a residual solid. Recrystallization from xylene afforded 8.0 g of a white solid. m.p. 129°–132° C.

EXAMPLE VI

Preparation of
2-[[N'-Methyl-N'-[N"-(1-naphthyloxycarbonyl)-N"-methylaminosulfenyl]-carbamoyloxy]]imino-3-methoxyimino-N,N-dimethylbutyramide A solution containing 1.7 g (0.012 m) of 1-naphthol, 4.2 g (0.012 m) of 2-[[N-methyl-N-[N'-fluorocarbonyl-N'-methylaminosulfenyl]carbamoyloxy]]-imino-N,N-dimethyl-3-methoxyiminobutyramide and 1.2 g (0.012 m) of triethylamine in 200 ml of toluene, was heated to 50° C. with stirring. After heating for 40 hrs. the solvent was removed under reduced pressure and the residue was taken in ethyl ether. The ether solution was washed with 2 percent sodium hydroxide and then with water until it was neutral. The ether layer was dried over anhydrous magnesium sulfate and concentrated to a solid residue. The solid was slurried with isopropyl ether and filtered to afford 4.0 g of a white solid m.p. 158°–160° C.

EXAMPLE VII

Preparation of
2-[[N'-Methyl-N'-[N"-(2,3-dihydro-2,2-dimethyl-7-benzofuranyloxycarbonyl)-N"-methylaminosulfenyl]carbamoyloxy]]imino-3-methoxyimino-N,N-dimethylbutyramide To a solution of 1.97 g (0.12 m) of 2,3-dihydro-2,2-dimethyl-7-hydroxybenzofuran and 4.2 g (0.012 m) of 2-[[N-methyl-N-[N'-fluorocarbonyl-N'-methylaminosulfenyl]carbamoyloxy]imino-N,N-dimethyl-3-methoxyiminobutyramide in 200 ml of toluene was added with stirring 1.2 g (0.012 m) of triethylamine. After heating the reaction mixture at 50° C. for 40 hours the solvent was removed under reduced pressure and the residual oil was taken in ethyl ether. The ether solution was washed with 2 percent sodium hydroxide and then with water until the wash was neutral. The organic layer was dried over magnesium sulfate and concentrated. The solid residue was recrystallized from isopropyl ether to afford 4.0 g of a white solid. m.p. 135°–136° C.

EXAMPLE VIII

Preparation of
2-[[N'-Methyl-N'-[N''-(4-nonylphenyloxycarbonyl)-N''-methylaminosulfenyl]carbamoyloxy]]imino-3-methoxyimino-N,N-dimethylbutyramide 2-[[N'-Methyl-N'-[N''-(4-nonylphenylsulfenyl)]carbamoyloxy]]imino-N,N-dimethyl-3-methoxyiminobutyramide was prepared as Example I by reacting 4.2 g (0.012 m) of 2-[[N'-methyl-N'-[N''-fluorocarbonyl-N''-methylaminosulfenyl]carbamoyloxy]]imino-N,N-dimethyl-3-methoxyiminobutyramide and 2.64 g (0.012 m) of 4-nonylphenol in 200 ml of toluene with 1.2 g (0.012 m) of triethylamine. After the work-up 6.0 g of the product was isolated as a residual oil.

NMR and IR were consistent with the proposed structure.

EXAMPLE IX

Preparation of
2-[[[N'-Methyl-N'-[[N''-[1-(N,N-dimethylaminocarbonyl)-2-methoxyiminopropylideneiminooxycarbonyl]-N''-methylaminosulfenyl]carbamoyloxy]]]imino-3-methoxyimino-N,N-dimethylbutyramide To a solution of 6.0 g (0321 m) of N,N-dimethyl-3-methoxyimino-2-oximinobutyramide and 2.96 g (0.0161 m) of N,N'-bis-(N-methyl-N-fluorocarbonylamino) sulfide in 75 ml of dioxane was added with stirring 3.25 g (0.321 m) of triethylamine. After stirring at room temperature for 20 hrs. the reaction mixture was concentrated under reduced pressure and the residual oil was taken in ethyl acetate. The organic solution was washed with water and dried over magnesium sulfate. On concentration it afforded 8.23 g of an oil which crystallized from isopropyl ether-hexane solution. m.p. 145°-147° C.

EXAMPLE X

Preparation of
2-[[[N'-Methyl-N'-[[N''-[1-(N,N-dimethylaminocarbonyl)-2-methoxyiminopropylideneiminooxycarbonyl]-N''-methylaminothiosulfenyl]]carbamoyloxy]]]imino-3-methoxyimino-N,N-dimethylbutyramide By employing the procedure used in Example IX, 6.0 g (0.0321 m) of N,N-dimethyl-3-methoxyimino-2-oximinobutyramide was reacted with 3.48 g (0.0161 m) of N,N'-bis-(N-methyl-N-flurorcarbonylamino) disulfide and 3.25 g (0.0321 m) of triethylamine in 75 ml of dioxane. Work-up afforded 8.9 g of a viscous oil. Purification by dry column chromatography afforded a solid as a mixture of isomers. m.p. 108°-114° C.

Selected species of the new compounds were evaluated to determine their pesticidal activity against mites, nematodes, and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in parts per million by weight employed in the tests described below were obtained by appropriate dilutions of the stock suspension with water. The test procedures were as follows:

Adults and nymphal stages of the bean aphid (Aphis fabae Scop.) reared on potted dwarf nasturtium plants at 65°-70° F. and 50±5 percent relative humidity, constituted with test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphids remaining on the plants were observed closely for movement and those which were unable to move the length of the body upon stimulation by prodding were considered dead.

Larvae of the southern armyworm (Spodoptera eridania, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty four hours, no more food was added. Larvae which were unable to move the length of the body, even upon stimulation by prodding, were considered dead.

Fourth instar larvae of the Mexican bean beetle (Epilachna varivestis, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for three days. Although the larvae could easily consume the leaf within 24 to 48 hours, no more food was added. Larvae which were unable to move the length of the body, even upon stimulation, were considered dead.

Four to six day old adult house flies (*Musca domestica*, L.), reared according to the specifications of the Chemical Specialties Manufacturing Association (Blue Book, McNair-Dorland Co., N.Y. 1954; pages 243-244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5 percent. Flies which showed no sign of movement on prodding were considered dead.

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds at the indicated dosage rate against aphid, mite, Southern Armyworm, Bean Beetle and house fly was rated as follows:

A = excellent control
B = partial control
C = no control
Dashes indicate no test conducted.

Experiments were also conducted to determine the phytotoxicity of representative compounds with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the foliage to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

Certain compounds were also evaluated to determine their peroral toxicity to mammals by conventional methods. The representative animal selected for this experiment was the rat. The test results obtained are expressed in terms of the number of milligrams of composition per kilogram of weight of the animal required to achieve a mortality rate of 50 percent ($LD_{50}$).

The results of these experiments are also summarized in Table I below.

NEMATODE TEST

The test organism used was the infective migratory larvae of the root-knot nematode, *Meloidogyne incognita* var. *acrita*, reared in the greenhouse on roots of cucumber plants. Infected plants were removed from the culture, and the roots are chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots; and the amount of galling visually rated.

The results of these tests are set forth in Table I below.

In the test for activity against nematode activity were rated as follows:
1 = severe galling, equal to untreated plants
2 = moderate galling
3 = light galling
4 = very light galling
5 = no galling, perfect control Dashes indicate no test conducted.

TABLE I

| | | BIOLOGICAL ACTIVITY | | | | | A.O. Rat | Phytotoxicity | | | | Nematode |
|---|---|---|---|---|---|---|---|---|---|---|---|---|
| Example # | Structure | Bean Aphid | 2-Spotted Mite | SAW | MBB | HF | mg/kg | Bean | Corn | Tomato | Cotton | Soybean | |
| 1 | CH₃ON=C(CH₃)–C(=O)–N(OC(=O)N(CH₃)–S–)–C₆H₄–C(CH₃)₂CH₃ with CN(CH₃)₂ | A | C | C | C | A | 30 | — | — | — | 1 | 1 | 1 |
| 2 | CH₃ON=C(CH₃)–C(=O)–CN(CH₃)₂, N-morpholino O–C(=O)–N(CH₃) | A | A | C | C | A | — | — | 1 | — | 1 | 1 | 1 |
| 3 | CH₃ON=C(CH₃)–C(=O)–CN(CH₃)₂, N–O–C(=O)–N(CH₃)–S–C(CH₃)₂CH₃ | A | A | C | B | A | 20 | 1 | 1 | 1 | 1 | 3 | 4 |
| 4 | CH₃ON=C(CH₃)–C(=O)–CN(CH₃)₂, N–O–C(=O)–N(CH₃)–S–N(CH₃)–C(=O)F | A | C | C | C | A | — | 1 | 1 | 1 | 1 | 2 | 1 |
| 5 | CH₃ON=C(CH₃)–C(=O)–CN(CH₃)₂, N–O–C(=O)–N(CH₃)–S–N(CH₃)–C(=O)–ON=C(CH₃)SCH₃ | A | B | A | A | A | 23.8 | 1 | 1 | 1 | 1 | 1 | 1 |

TABLE I-continued

| Example # | Structure | BIOLOGICAL ACTIVITY ||||||| A.O. Rat mg/kg | Phytotoxicity ||||| Nematode |
|---|---|---|---|---|---|---|---|---|---|---|---|---|---|---|
| | | Bean Aphid | 2-Spotted Mite | SAW | MBB | HF | | | Bean | Corn | Tomato | Cotton | Soybean | |
| 6 | CH₃ON O ‖ ‖ CH₃—C—C—CN(CH₃)₂ ‖ N—O—C—N—S—C—(1-naphthyl) ‖ ‖ O CH₃ O CH₃ | A | C | A | A | C | 160 | — | 1 | — | 1 | 1 | 1 |
| 7 | CH₃ON O ‖ ‖ CH₃—C—C—CN(CH₃)₂ ‖ N—O—C—N—S—C—(2,2-dimethylchroman-8-yl) ‖ ‖ O CH₃ O CH₃ | A | B | A | A | A | 10 | — | 1 | — | 1 | 1 | 3 |
| 8 | CH₃ON O ‖ ‖ CH₃—C—C—CN(CH₃)₂ ‖ N—O—C—N—S—C—O—(4-C₉H₁₉-phenyl) ‖ ‖ O CH₃ O CH₃ | A | B | C | C | A | >800 | — | 1 | — | 1 | 1 | 1 |

TABLE I-continued

| Example # | Structure | BIOLOGICAL ACTIVITY | | | | | A.O. Rat mg/kg | Phytotoxicity | | | | Nematode |
| --- | --- | --- | --- | --- | --- | --- | --- | --- | --- | --- | --- | --- |
| | | Bean Aphid | 2-Spotted Mite | SAW | MBB | HF | | Bean | Corn | Tomato | Cotton | Soybean | |
| 9 | $\left\{ \begin{array}{c} CH_3ON \\ \| \\ CH_3-C-C=N-O-C-N-S-CH_3 \\ \| \ \| \ \| \\ O \ \ CN(CH_3)_2 \ \ O \end{array} \right\}_2$ | A | C | C | A | A | 25.2 | 1 | 1 | 2 | 1 | 2 | 4 |
| 10 | $\left\{ \begin{array}{c} CH_3ON \\ \| \\ CH_3-C-C=N-O-C-N-S-CH_3 \\ \| \ \| \ \| \\ O \ \ CN(CH_3)_2 \ \ O \end{array} \right\}_2$ | A | A | C | B | A | — | 1 | 1 | 1 | 1 | 1 | 3 |

It will be understood that the insect species and other pests employed in the above tests are merely representative of a wide variety of pests that can be controlled by use of the novel compounds of this invention.

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein control the attack by insects, acarides, especially mites, and nematodes, upon plants or other material to which the pesticides are applied. With respect to plants, they have a high margin of safety in that when used in sufficient amount to kill or repel the insects, they do not burn or injure the plant to any appreciable degree, and they resist weathering which includes wash-off caused by rain, decomposition by ultra-violet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. Mixtures of the active compounds may be employed if desired as well as combinations of the active compounds of this invention with other biologically active compounds.

What is claimed is:

1. A compound of the formula:

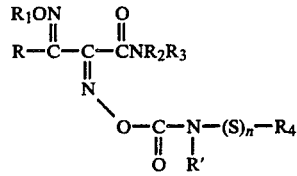

wherein:

$n = 1$ or $2$;

$R$, $R'$, $R_1$, $R_2$, and $R_3$ are individually alkyl groups of one to four carbon atoms;

$R_4$ is: piperidino, pyrrolidino or morpholino group each of which may be unsubstituted or substituted with one or two alkyl groups.

2. A pesticidal composition comprising an acceptable carrier and as the active toxicant an acaricidally, nematocidally or insecticidally effective amount of at least one compound of claim 1.

3. A method of controlling insects, acarids and nematodes which comprises subjecting the insects, acarids or nematodes to an insecticidally, acaricidally or nematocidally effective amount of a compound of claim 1.

* * * * *